United States Patent [19]
Gia

[11] Patent Number: 5,690,667
[45] Date of Patent: Nov. 25, 1997

[54] VASOOCCLUSION COIL HAVING A POLYMER TIP

[75] Inventor: Son M. Gia, San Jose, Calif.

[73] Assignee: Target Therapeutics, Fremont, Calif.

[21] Appl. No.: 721,351

[22] Filed: Sep. 26, 1996

[51] Int. Cl.$^6$ .................................................. A61B 17/00
[52] U.S. Cl. ................................ 606/191; 606/200
[58] Field of Search ........................... 606/108, 191, 606/194, 200; 604/104, 52

[56] References Cited

U.S. PATENT DOCUMENTS

| | | | |
|---|---|---|---|
| 4,735,201 | 4/1988 | O'Reilly | 128/303 |
| 4,994,069 | 2/1991 | Ritchart et al. | 606/191 |
| 5,122,136 | 6/1992 | Guglielmi et al. | 606/32 |
| 5,234,437 | 8/1993 | Sepetka | 606/108 |
| 5,250,071 | 10/1993 | Palermo | 606/198 |
| 5,261,916 | 11/1993 | Engelson | 606/108 |
| 5,304,194 | 4/1994 | Chee et al. | 606/191 |
| 5,304,195 | 4/1994 | Twyford, Jr. et al. | 606/191 |
| 5,312,415 | 5/1994 | Palermo et al. | 606/108 |
| 5,350,397 | 9/1994 | Palermo et al. | 606/200 |
| 5,354,295 | 10/1994 | Guglielmi et al. | 606/32 |
| 5,382,259 | 1/1995 | Phelps et al. | 606/151 |
| 5,413,586 | 5/1995 | Dibie et al. | 606/200 |
| 5,423,829 | 6/1995 | Pham et al. | 606/108 |
| 5,476,472 | 12/1995 | Dormandy, Jr. et al. | 606/151 |

Primary Examiner—Gary Jackson
Attorney, Agent, or Firm—Morrison & Foerster, LLP

[57] ABSTRACT

A vasoocclusive helical metal coil having a thermoplastic polymer plug in at least one of its ends that has been melted so that it molds to the coil windings and insulates and blunts the end(s).

11 Claims, 3 Drawing Sheets 5,690,667

VASOOCCLUSION COIL HAVING A POLYMER TIP

TECHNICAL FIELD

This invention is in the field of vasoocclusion devices. More particularly, it relates to a vasoocclusion coil having a polymer tip.

BACKGROUND

Vasoocclusion devices are surgical implements that are placed within vessels, typically via a catheter, to block the vessel or to fill a vascular cavity such as an aneurysm. One type of vasoocclusion device is in the form of a helical wire coil. The coil may have a cylindrical, conical or other shaped envelope and may be formed into a secondary shape if desired. See U.S. Pat. No. 4,994,069. The coil may have fibers attached to it to facilitate embolization. See U.S. Pats. Nos. 5,304,194, 5,476,472 and 5,382,259. The coil may be free (unattached) and placed at the desired vascular site by displacing it from the end of a catheter. Alternatively, the coil may be removably attached to the distal end of a wire or fiber, placed at the desired site, and detached from the wire by mechanical, electrolytic, or thermal means. See U.S. Pats. Nos. 4,735,201, 5,354,295 and 5,250,071.

One or both ends of the coil may be blunted to make it/them less likely to abrade or puncture the vessel. The "blunting" is typically accomplished by either melting the end or by soldering a bead of metal onto the end. Commonly owned copending U.S. application Ser. No. 08/499,525, filed Jul. 7, 1995, describes a coil having a polymer plug or insert in its distal end. The coil described in this copending application is used to transmit radiofrequency energy into the vessel to cause the vessel wall to collapse. The polymer plug in the distal end of the coil insulates the tip of the coil and lessens the likelihood that the distal tip will erode or perforate the vessel wall.

A principal object of the present invention is to provide an easier and effective way to blunt and or insulate one or both ends of a vasoocclusive coil.

DISCLOSURE OF THE INVENTION

One aspect of the invention is a vasoocclusive coil comprising a helical coil having a multiplicity of windings that define a lumen, a first end, and a second end, and a plug of thermoplastic polymer comprised of a first portion that extends into the lumen at said first end and is molded into the windings defining said first end and a second rounded portion that extends axially outwardly from said lumen at said first end.

Another aspect is a method for blunting or insulating an end of a vasoocclusive coil comprising:

(a) providing a helical metal coil having a multiplicity of windings that define a lumen, a first end, and a second end;

(b) placing a first portion of a biocompatible thermoplastic polymer strand into the lumen at said first end with a second portion of said strand extending axially outwardly of the lumen at said first end;

(c) melting the polymer strand to cause said first portion to mold to the windings defining said first end and said second portion to be formed into a rounded protuberance; and (d) cooling the polymer strand to cause the strand to solidify.

BRIEF DESCRIPTION OF THE DRAWINGS

In the drawings, which are not to scale.

MODES FOR CARRYING OUT THE INVENTION

Figure 1:
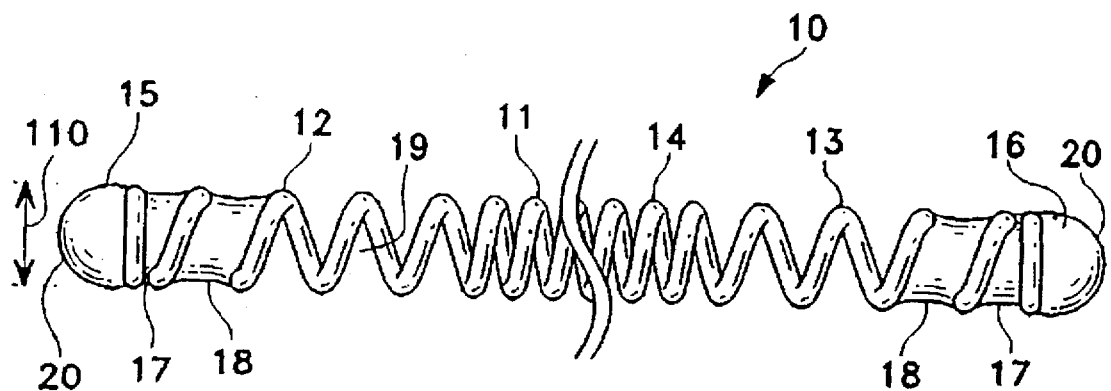
FIG. 1 is an elevational view of one embodiment of the invention in which a helical coil is blunted at one end.

FIG. 1 depicts one embodiment, generally designated 10 of a vasoocclusive coil of this invention. Coil 10 has a multiplicity of helical windings 11. The windings of the end segments, generally designated 12 and 13 of the coil have a longer pitch than the windings of the central segment 14. The coil has two free ends, generally designated 15 and 16, each of which is blunted by a plug 17 of a biocompatible thermoplastic polymer. As depicted, plug 17 has an inner section 18 that extends into the lumen 19 defined by the windings and an outer portion 20 that extends outwardly from the lumen and defines a rounded blunt protuberance. The inner section 18 is thermally molded to the windings; that is, it at least partly surrounds the windings and conforms to the shape of the windings. In such structure, the plug is less likely to loosen or disengage from the windings than the structure shown in U.S. Ser. No. 08/499,525. The inner section will normally extend about 1 to 5 windings into the lumen 19, preferably about 2–4 windings.

The windings of coil 10 will typically be made of a metal such as platinum, gold, rhodium, rhenium, palladium, tungsten, and the like or alloys of such metals. These metals have significant radiopacity and their alloys may be tailored to provide desired degrees of stiffness and flexibility. The windings may be made of other suitable biocompatible materials such as polymers or composites of metals and polymers.

Figure 4:
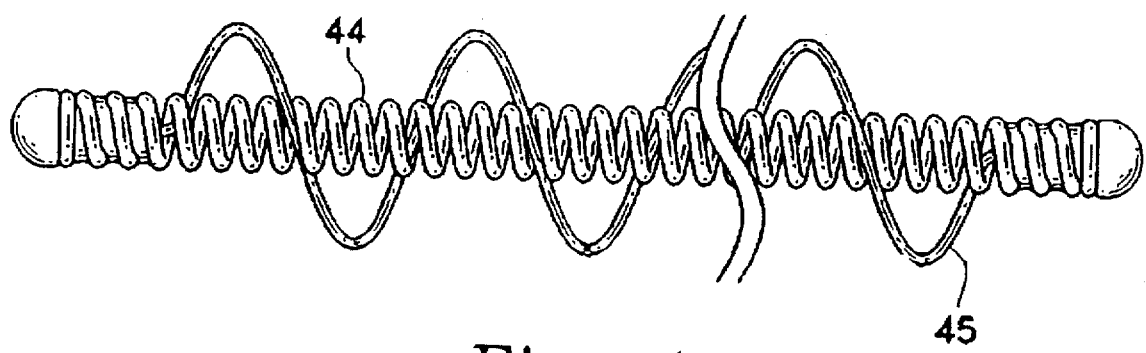
FIG. 4 is an elevational view of another embodiment of the invention wherein the coil includes a radially extending fibrous element.

While the cross-section of the windings of FIG. 1 is circular, windings having other cross-sectional shapes, e.g. elliptical, trapezoidal, rhombic, rectangular, square, may be used. Circular cross sectional windings will typically have a diameter of about 0.01 to about 0.15 mm. Correspondingly, the diameter of the helix formed by the windings will normally be in the range of about 0.2 to 0.8 mm. For neurovascular use the diameter of the helix will typically be in the range of 0.3 to 0.5 mm. While the helix is shown as having a uniform diameter along the length of the coil, helixes having a varying diameter over a portion or the entire length of the helix or helixes having segments of different diameter may also be used. Similarly, the pitch of the windings may be uniform, as shown in FIG. 4, or may vary over a portion or the entire length of the coil. The axial length of the coil will usually be in the range of 0.5 to 100 cm, more usually 2 to 40 cm. The coil will typically have 10 to 75 windings per cm, more usually 10 to 40 windings per cm. It will be appreciated that the above described dimensions are not critical and that dimensions that are suitable for occluding vascular sites within the human body are intended.

The plug 17 is made of a thermoplastic, biocompatible polymer such as a polyester (e.g. Dacron), polyamide (e.g. Nylon), or polyolefin (e.g., polypropylene). Typically the polymer will melt at temperatures above about 125° C. The plug is formed by initially placing a rod or strand of the polymer into the lumen of the coil, leaving a portion (typically about 0.1 to 3 mm) of the rod or strand extending outwardly from the coil end. The plug is then heated to above the melt temperature of the polymer causing the portion of the rod within the lumen to flow and mold to the coil windings and the portion of the rod outside the lumen to form into a rounded bead or protuberance. The plug is then cooled to solidify the polymer.

Figure 2:
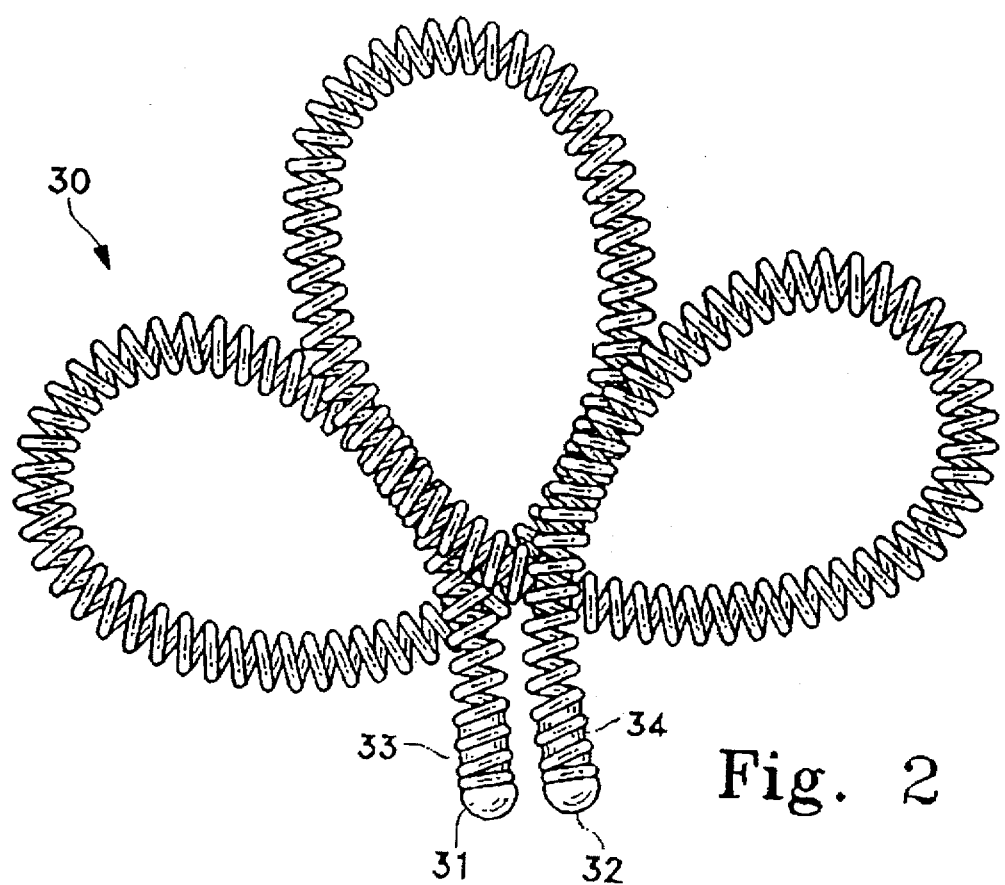
FIG. 2 is an elevational view of another embodiment of the invention in which a helical coil having a secondary shape is blunted at both ends.

FIG. 2 depicts another embodiment, generally designated 30, of a vasoocclusive coil of the invention. Coil 30 has a similar structure to coil 10 except that the former has a uniform pitch and a clover leaf secondary shape. As depicted, the ends 31, 32 of coil 30 are blunted with polymer plugs or tips 33, 34.

Figure 3:
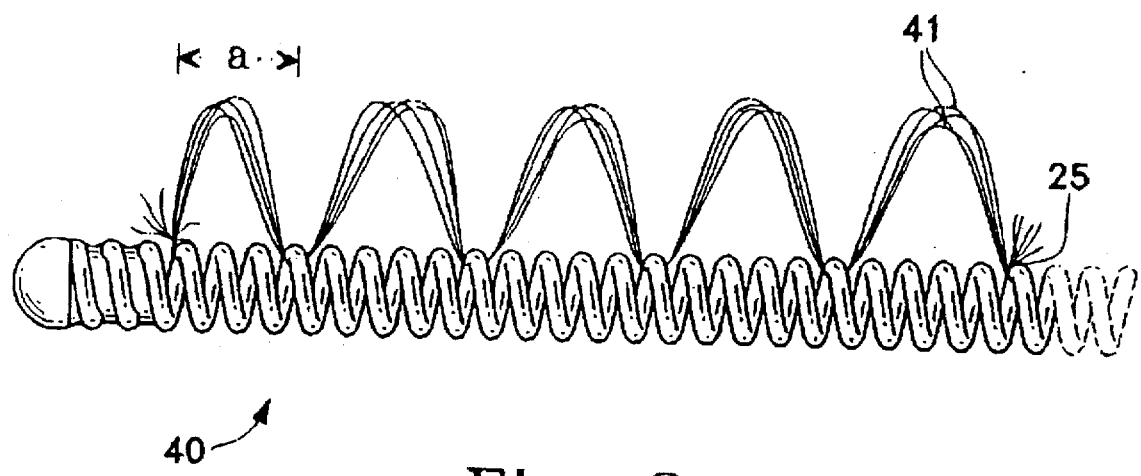
FIG. 3 is an elevational view of a third embodiment of the invention in which the helical coil has a multiplicity of fibrous elements attached to it.

FIG. 3 shows a third embodiment, generally designated 40, of a vasoocclusive coil of the invention. Coil 40 has a similar structure to coil 10 except that the former has a uniform pitch and includes a plurality of fibers 41 attached to the coil windings. As shown, end 42 of coil 40 is blunted with a polymer plug 43.

FIG. 4 shows a coil 44 that is identical in structure to the coil of FIG. 1 except that a strand 45 of polymer extends sinusoidally the length of the coil with its respective ends fused to and integral with the polymer tips. As shown, the strand is composed of loops that extend radially outwardly of the coil windings and extend through the coil windings at spaced intervals.

The vasoocclusive coils of the invention are particularly useful in devices, such as those described in U.S. Ser. No. 08/499,525, filed Jul. 7, 1995, that are used to deliver radiofrequency energy intravascularly. The coil may be nondetachable or detachable by electrolytic means such as described in U.S. Pat. No. 5,122,136 or by mechanical means such as described in U.S. Pat. Nos. 5,234,437; 5,250,071; 5,261,916; 5,304,195; 5,312,415; and 5,350,397.

Figure 5:
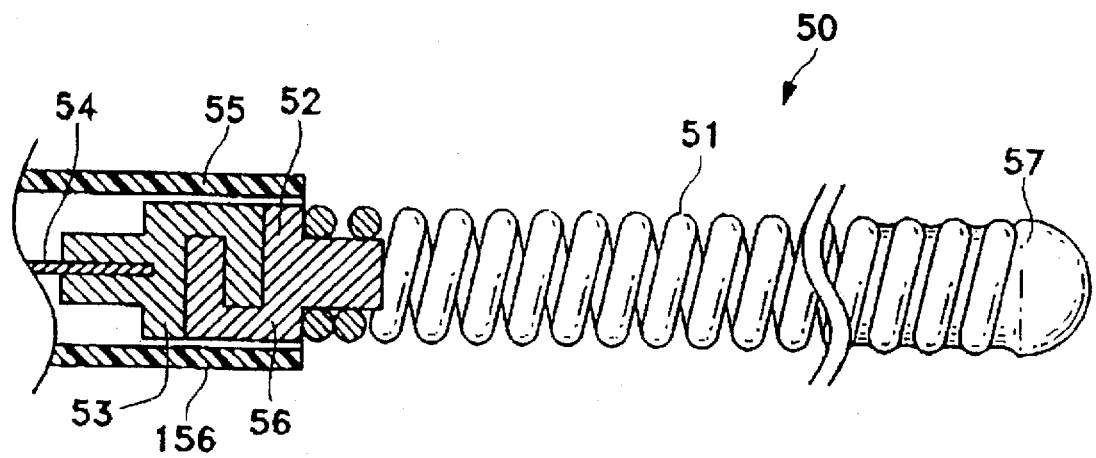
FIG. 5 is an elevational view of a fourth embodiment of the invention in which the helical coil is adapted to be mechanically released from the distal end of a wire.

FIG. 5 depicts an embodiment, generally designated 50, having a coil 51 that may be detached through operation of a connective joint 52. Joint 52 has a clasp section 53 which remains attached to a core wire 54 when sheath or catheter body 55 is retracted proximally. Joint 52 also includes a second clasp section 56 that is carried on the proximal end of coil 51 and interlocks with clasp section 53 when the assembly is within sheath 55. When the sheath is withdrawn from about the assembly, the clasp sections are free to disengage, thus detaching coil 51. As shown, the distal end of coil 51 has a polymer plug 57 that blunts and insulates the distal end. Core wire 51 may be electrically connected to a source of radiofrequency energy.

Figure 6:
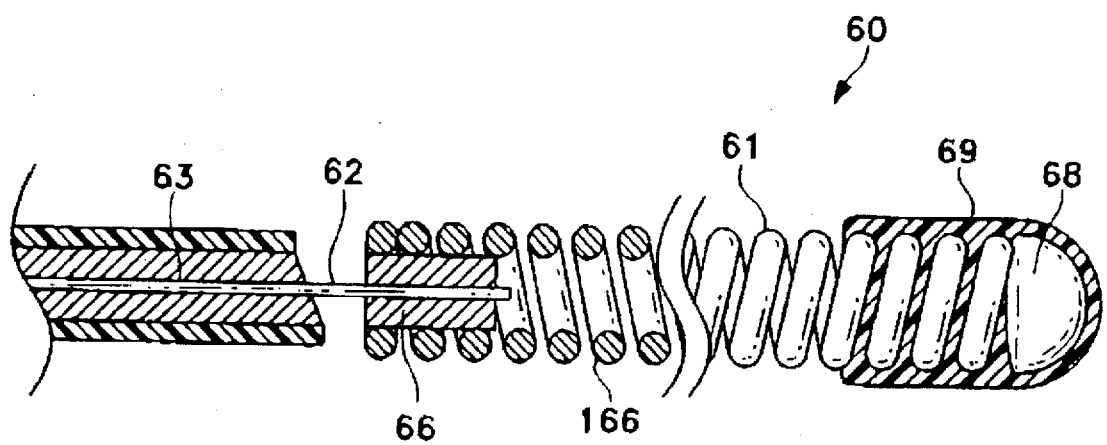
FIG. 6 is an elevational view of a fifth embodiment of the invention in which the helical coil is adapted to be electrolytically released from the distal end of a wire.

FIG. 6 shows an embodiment, generally designated 60, having a coil 61 that may be detached through operation of a connective joint 62 that is susceptible to electrolysis. Such joints are described in detail in U.S. Pat. No. 5,423,829. Joint 62 is made of a metal which, upon application of a suitable voltage to a core wire 63, will erode in the bloodstream, thereby allowing coil 61 to detach. Coil 61 is made of a metal that is more "noble" in the electromotive series than the metal of joint 62. A return electrode (not shown) is supplied to complete the circuit. The region of core wire 63 proximal to the joint is insulated to focus the erosion at the joint. An electrically conductive bushing 66 is used to connect the distal end of core wire 63 to the proximal end of coil 61. A polymer plug 68, similar in structure to the previously described plugs, is molded into the distal end of the coil. In addition, the exterior surface of the distal windings of the coil is encased in a thermoplastic polymer sheath 69. As shown, the polymer sheath is molded to the windings and is integral with the plug 68. This structure may be formed by placing a thermoplastic sheath about the distal windings, placing a strand of thermoplastic polymer in the distal end of the coil, and heating the distal end of the coil to cause the sheath and strands to melt, fuse together, and mold to the interior and exterior surfaces of the windings.

All U.S. patents referred to above are hereby incorporated in their entireties by reference.

I claim:

1. A vasoocclusion coil comprising a helical coil having a multiplicity of windings that define a lumen, a first end and a second end, and a plug of thermoplastic biocompatible polymer comprised of a first portion that extends into the lumen at said first end and is molded into the windings defining said first end and a second rounded portion that extends axially outwardly from said lumen at said first end.

2. The vasoocclusion coil of claim 1 wherein the polymer is a polyester.

3. The vasoocclusion coil of claim 1 wherein the windings are made of metal.

4. The vasoocclusion coil of claim 1 wherein said first portion extends 1 to 5 windings into the lumen.

5. The vasoocclusion coil of claim 1 including a sheath of a thermoplastic biocompatible polymer that encases and is molded to the exterior surface of the windings defining the first end.

6. The vasoocclusion coil of claim 1 further comprising a strand of said polymer having a first end connected to the first portion of the plug, a second end, and a segment intermediate said first and second ends that extends axially along the coil in a generally serpentine configuration composed of loops that extend through the coil windings at spaced intervals.

7. The vasoocclusion coil of claim 1 further comprising a second plug of thermoplastic biocompatible polymer comprised of a first portion that extends into the lumen at said second end of the coil and is molded into the windings defining said second end and a second rounded portion that extends axially outwardly from said lumen at said second end.

8. The vasoocclusion coil of claim 7 comprising a strand of a biocompatible polymer having a first end connected to said first plug, a second end connected to said second plug, and a segment intermediate said first and second ends of the strand that extends axially along the coil in a generally serpentine configuration composed of loops that extend through the coil windings at spaced intervals.

9. An assembly for use in occluding a vessel or vascular cavity comprising:

(a) a wire having a distal end;

(b) the vasoocclusion coil of claim 1 wherein the distal end of the wire is detachably coupled to the second end of the coil.

10. The assembly of claim 9 wherein the distal end of the wire is coupled to the second end of the coil by a mechanically detachable joint.

11. The assembly of claim 9 wherein the distal end of the wire is coupled to the second end of the coil by a metal joint that is susceptible to electrolysis.

* * * * *